(12) United States Patent
Kiyota et al.

(10) Patent No.: US 8,192,983 B2
(45) Date of Patent: Jun. 5, 2012

(54) INCUBATOR

(75) Inventors: Yasujiro Kiyota, Tokyo (JP); Takayuki Uozumi, Tokyo (JP); Nobuhiko Maiya, Yokohama (JP); Hirofumi Shiono, Fujisawa (JP)

(73) Assignee: Nikon Corporation, Tokyo (JE)

( * ) Notice: Subject to any disclaimer, the term of this patent is extended or adjusted under 35 U.S.C. 154(b) by 1020 days.

(21) Appl. No.: 11/921,874

(22) PCT Filed: Jun. 23, 2006

(86) PCT No.: PCT/JP2006/312618
§ 371 (c)(1),
(2), (4) Date: Dec. 10, 2007

(87) PCT Pub. No.: WO2007/004445
PCT Pub. Date: Jan. 11, 2007

(65) Prior Publication Data
US 2009/0098642 A1    Apr. 16, 2009

(30) Foreign Application Priority Data
Jul. 1, 2005 (JP) ................. 2005-194197

(51) Int. Cl.
C12M 1/00 (2006.01)
C12M 3/00 (2006.01)

(52) U.S. Cl. ............. 435/303.1; 435/286.1; 435/286.2

(58) Field of Classification Search .... 435/286.1–286.6, 435/288.7, 293.1, 303.1–303.3, 287.3, 809
See application file for complete search history.

(56) References Cited

U.S. PATENT DOCUMENTS

| | | | |
|---|---|---|---|
| 2003/0040104 A1* | 2/2003 | Barbera-Guillem | 435/286.2 |
| 2004/0152188 A1* | 8/2004 | Yamamoto et al. | 435/287.3 |
| 2006/0093514 A1* | 5/2006 | Dawes | 422/44 |

FOREIGN PATENT DOCUMENTS

| | | |
|---|---|---|
| CN | 1502687 A | 6/2004 |
| JP | A 59-66878 | 4/1984 |
| JP | A 7-236468 | 9/1995 |
| JP | A 11-9265 | 1/1999 |
| JP | A 2004-180675 | 7/2004 |
| JP | A 2005-6507 | 1/2005 |

OTHER PUBLICATIONS

Office Action issued in Chinese Patent Application No. 200680023989.1, dated Jan. 26, 2011 (w/English-language Translation).

* cited by examiner

*Primary Examiner* — Michael Marcheschi
*Assistant Examiner* — Shanta G Doe

(74) *Attorney, Agent, or Firm* — Oliff & Berridge, PLC

(57) ABSTRACT

An incubator including a temperature-controlled room adjusted to a predetermined environment condition for culturing a sample of an incubation container at inside of the temperature-controlled room, the incubator including a shifting mechanism for moving a position of the incubation container at inside of the temperature-controlled room by a motor, a temperature adjusting section for adjusting a temperature at inside of the temperature-controlled room, an operating information generating section for generating operating information with regard to a position of operating and a time period of operating the motor prior to operating the motor, an estimated variation outputting section for outputting an estimation variation of a temperature state by operating the motor based on the operating information, and a controlling section for controlling the temperature adjusting section to cancel a temperature change of an amount of the estimated variation in synchronism with operating the motor.

9 Claims, 9 Drawing Sheets

INCUBATOR

CROSS-REFERENCE TO RELATED APPLICATION

This application is a U.S. National Stage application claiming the benefit of prior filed International Application Number PCT/JP2006/312618, filed Jun. 23, 2006, in which the International Application claims a priority date of Jul. 1, 2005 based on prior filed Japanese Application Number 2005-194197 the entire contents of which are incorporated herein by reference.

TECHNICAL FIELD

The present invention relates to an incubator for culturing a sample of an incubation container at inside of a temperature-controlled room adjusted to a predetermined environment condition.

BACKGROUND ART

In a background art, there is generally used an incubator having a temperature-controlled room for culturing respective kinds of microbes or cells. Generally, a temperature-controlled room of an incubator is arranged with a sensor for detecting a current value of an environment condition (for example, temperature, humidity, carbon dioxide concentration, oxygen concentration, nitrogen concentration or the like), and an environment adjusting apparatus for adjusting the above-described respective parameters, and inside of the temperature-controlled room is adjusted to a predetermined environment condition.

Further, Patent Document 1 discloses an incubator having an apparatus of carrying an incubation container and a microscope unit at inside of a temperature-controlled room, carrying in and out the incubation container to and from a carrying in/out entrance having an automatic door and automatically carrying the incubation container or observing a sample or the like at inside of the temperature-controlled room.

According to the incubator of Patent Document 1, a heat source of a motor of the carrying apparatus, an illuminating light source of the microscope unit or the like is arranged at inside of the temperature-controlled room, and therefore, a temperature at inside of the temperature-controlled room rises when the incubation container is carried or the sample is observed. Further, when the incubation container is carried in and out to and from the carrying in/out entrance, an environment condition at inside of the temperature-controlled room is varied by opening and closing the automatic door.

However, according to the incubator of the background art, when a variation in the environment condition is brought about owing to operation of the apparatus, the environment adjusting apparatus is not operated until a change equal to or larger than a threshold is detected in a parameter of the environment condition and there is a room for improvement in that a comparatively large nonuniformity is liable to be brought about in the environment condition at inside of the temperature-controlled room.

Patent Document 1: Japanese Unexamined Patent Application Publication No. 2004-180675

DISCLOSURE

Problems to be Solved

The invention is for resolving the above-described problem of the background art and it is an object thereof to provide an incubator capable of remarkably restraining an environment condition owing to operation of an apparatus constituting an environment varying factor at inside of a temperature-controlled room.

Means for Solving the Problems

A first aspect of the invention having an incubator including a temperature-controlled room adjusted to a predetermined environment condition and culturing a sample of an incubation container at inside of the temperature-controlled room, the incubator including a shifting mechanism moving a position of the incubation container at inside of the temperature-controlled room by a motor, a temperature adjusting section adjusting a temperature at inside of the temperature-controlled room, an operating information generating section generating operating information with regard to a position of operating and a time period of operating the motor prior to operating the motor, an estimated variation outputting section outputting an estimated variation of a temperature state by operating the motor based on the operating information, and a controlling section controlling the temperature adjusting section to cancel a temperature change of an amount of the estimated variation in synchronism with operating the motor.

A second aspect of the invention in which a plurality of the temperature adjusting sections are arranged at positions at inside of the temperature-controlled room different from each other and the controlling section changes outputs of the respective temperature adjusting sections independently from each other based on a position of operating the motor in the first aspect of the invention.

A third aspect of the invention in which the position of operating the motor is changed by an operation of the shifting mechanism and the controlling section changes the outputs of the respective temperature adjusting sections independently from each other based on a change in the position of operating the motor in the second aspect of the invention.

A fourth aspect of the invention having an incubator including a temperature-controlled room adjusted to a predetermined environment condition and culturing a sample of an incubation container at inside of the temperature-controlled room, the incubator including an illuminating light source illuminating the incubation container at inside of the temperature-controlled room, a temperature adjusting section adjusting a temperature at inside of the temperature-controlled room, an operating information generating section generating operating information with regard to an illumination time period of the illumination light source prior to operating the illuminating light source, an estimated variation outputting section outputting an estimated variation of a temperature state by operating the illuminating light source based on the operating information, and a controlling section controlling the temperature adjusting section to cancel a temperature change of an amount of the estimated variation in synchronism with operating the illuminating light source.

A fifth aspect of the invention in which a plurality of the temperature adjusting sections are arranged at positions at inside of the temperature-controlled room different from each other and the temperature adjusting section arranged at a region at a vicinity of the illuminating light source is set to be higher in a temperature changing function than at other positions in the fourth aspect of the invention.

A sixth aspect of the invention in which the estimated variation outputting section is configured by either one of a recording section recorded with a corresponding relationship between the operation information and the estimated variation, and a calculating section of calculating the estimated variation based on the operation information in any of the first through the fifth aspects of the invention.

A seventh aspect of the invention having an incubator including a temperature-controlled room adjusted to a predetermined environment condition and culturing a sample of an incubation container at inside of the temperature-controlled room, the incubator including a carrying in/out entrance carrying in and out the incubation container to and from inside of the temperature-controlled room, an automatic door opening and closing the carrying in/out entrance, an environment parameter adjusting section adjusting an environment parameter selected from any one of a temperature, a humidity, a carbon dioxide concentration, an oxygen concentration and a nitrogen concentration at inside of the temperature-controlled room, a first sensor section acquiring a value of the environment parameter on an inner side of the temperature-controlled room, a second sensor section acquiring the value of the environment parameter on an outer side of the temperature-controlled room, an operating information generating section generating operating information with regard to a time period of opening the automatic door prior to operating to open the automatic door, an estimated variation outputting section outputting an estimated variation of the environment parameter by opening the automatic door based on a difference of the environment parameters between inside and outside of the temperature-controlled room and the operating information, and a controlling section controlling the environment parameter adjusting section to chancel a change in the environment parameter of an mount of the estimated variation in synchronism with operating the automatic door.

An eighth aspect of the invention in which the estimated variation outputting section is configured by either one of a recording section recorded with a difference of the environment parameters between inside and outside of the temperature-controlled room and a corresponding relationship between the operating information and the estimated variation, and a calculating section calculating the estimated variation based on the difference of the environment parameters between inside and outside of the temperature-controlled room and the operating information in the seventh aspect of the invention.

EFFECT

According to the invention, the environment parameter of the temperature or the like is adjusted to cancel the change in the amount of the estimated variation in synchronism with operating apparatus for bringing about the variation in the environment condition and the variation in the environment condition at inside of the incubator is remarkably restrained.

DETAILED DESCRIPTION OF THE EMBODIMENTS (Explanation of First Embodiment)

Figure 1:
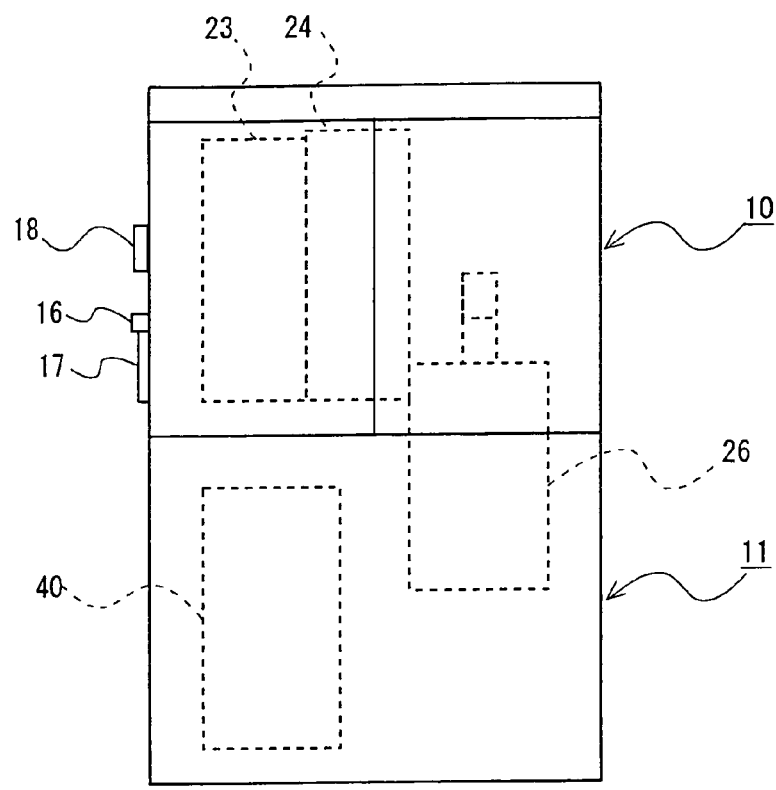
FIG. 1 is a front view of an incubator according to a first embodiment.
Figure 2:
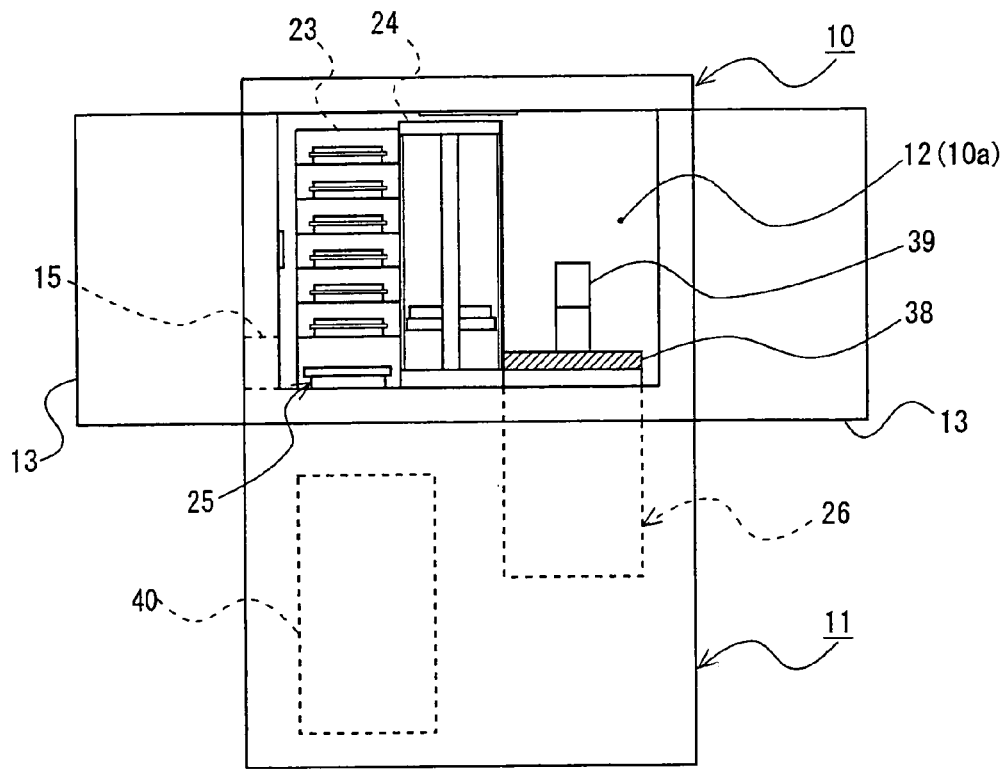
FIG. 2 is a view showing a state of opening a front door of a first cabinet in FIG. 1.

FIG. 1 and FIG. 2 are outline front views showing a total constitution of an incubator according to a first embodiment. The incubator is configured by a first cabinet 10 and a second cabinet 11.

The first cabinet 10 is mounted to an upper side of the second cabinet 11. Inside of the first cabinet 10 is formed with a temperature-controlled room 12 covered by an insulating member. A front face side of the first cabinet 10 constitutes an opening portion 10a. Further, the opening portion 10a is closed openably/closably by a biparting front door 13. Further, a carrying in/out entrance 15 capable of passing an incubation container 14 (well plate, flask, dish or the like) is formed proximate to a lower side of a left side face of the first cabinet 10. The carrying in/out entrance 15 is closed openably/closably by an automatic door 17 slid by a driving mechanism 16. Further, a bottom face of the first cabinet 10 is formed with an opening 10b for arranging a microscope unit 26 described later at a position proximate to a right side in view from a front face. Further, an outer side of the first cabinet 10 is arranged with an external sensor 18 for detecting a value of an environment parameter (for example, temperature, humidity, carbon dioxide concentration, oxygen concentration, nitrogen concentration or the like) at outside of the temperature-controlled room 12.

Figure 3:
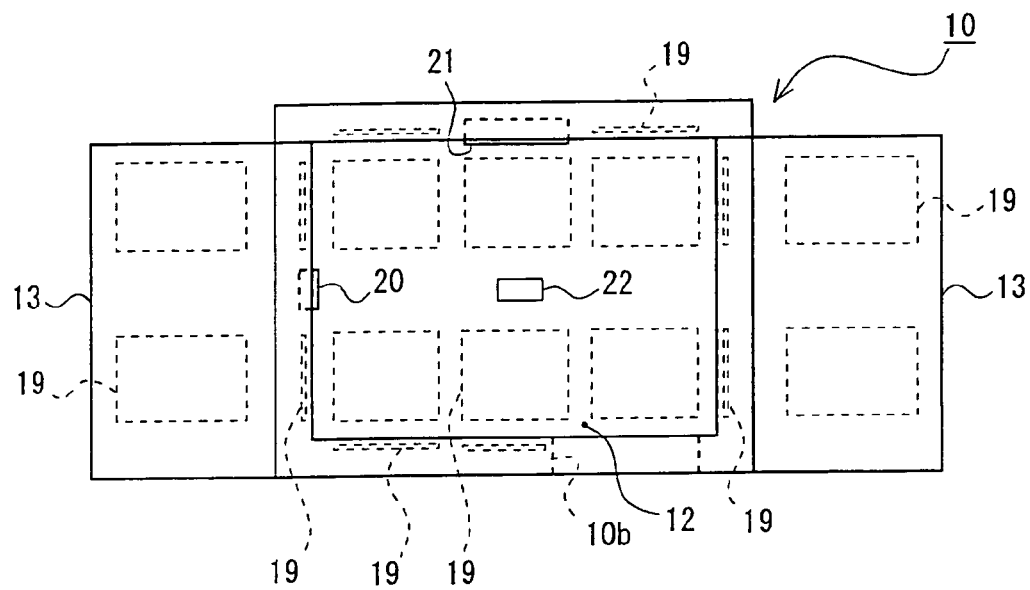
FIG. 3 is a front view showing a constitution of inside of a temperature-controlled room.

FIG.3 is a front view showing a constitution of inside of the temperature-controlled room. Respective wall faces of the first cabinet 10 include a plurality of environment adjusting apparatus having Pertier elements. The environment adjusting apparatus carries out heating or cooling by a Pertier effect by inverting electricity conducting polarities of the Pertier element. An example of an environment adjusting apparatus includes a temperature adjusting apparatus 19. Further, the respective temperature adjusting apparatus 19 can carry out a temperature control independently from each other. Further, at a periphery of region of arranging the microscope unit 26 disposed at a right lower corner of the temperature-controlled room 12 in FIG.2, heat is liable to be confined more than at other positions by generating heat by the microscope unit 26. Therefore, according to the first embodiment, a heating function and a cooling function of the temperature adjusting apparatus 19 at a vicinity of the region of arranging the microscope unit are set to be higher than those of the temperature adjusting apparatus 19 at other positions.

Further, a left side face of inside of the temperature-controlled room 12 is arranged with a spraying apparatus 20 for adjusting humidity. Further, an upper face of inside of the temperature-controlled room 12 is arranged with a gas introducing section 21. The gas introducing section 21 is connected with a carbon dioxide bomb, an oxygen bomb and a nitrogen bomb (illustration of bombs is omitted). Further, the gas introducing section 21 introduces gases from respective bombs to the temperature-controlled room 12 to adjust a carbon dioxide concentration, an oxygen concentration and a nitrogen concentration at inside of the temperature-controlled room 12. Further, an inner side of the temperature-controlled room 12 is arranged with an internal sensor 22 for detecting values of environment parameters at inside of the temperature-controlled room 12.

A stocker 23, a container shifting mechanism 24, a container carrying in/out mechanism 25 and the microscope unit 26 are contained at inside of the temperature-controlled room 12 of the first cabinet 10.

Figure 4:
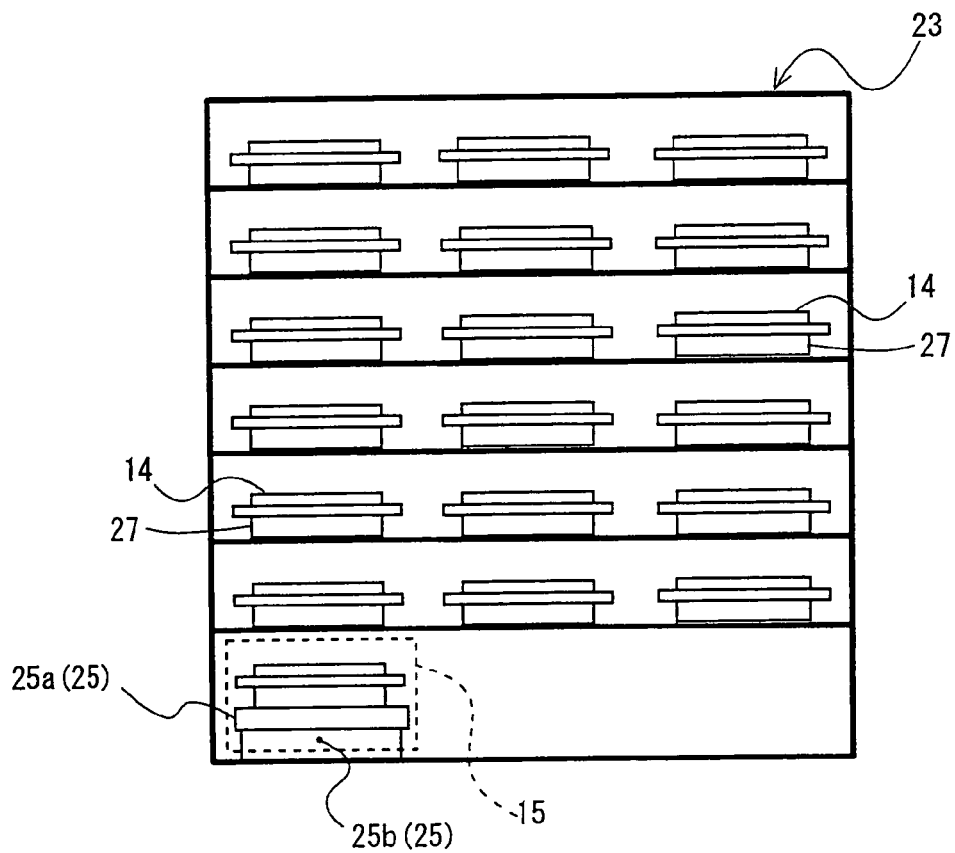
FIG. 4 is a view showing a container containing state of a stocker from a direction of a side face of a cabinet.
Figure 5:
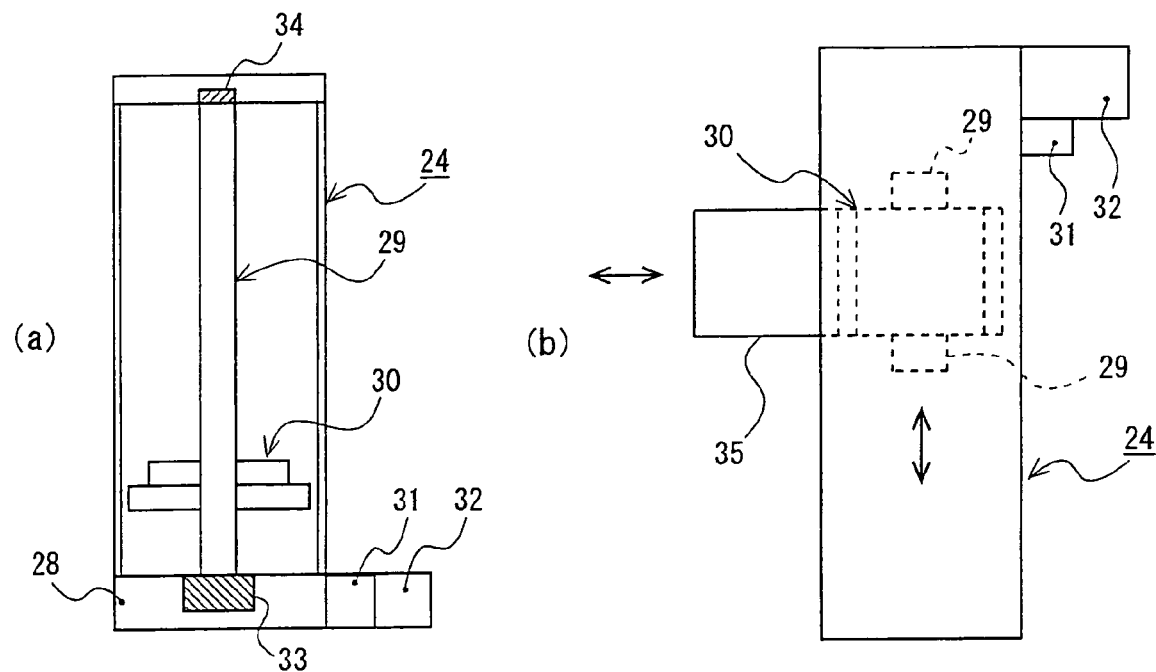
FIG. 5 shows (a) an outline view of a container carrying mechanism from a direction of a front face of a cabinet, and (b) an outline view of the container carrying mechanism from a direction of a plane of the cabinet.

The stocker 23 is arranged on a left side of inside of the temperature-controlled room 12 in view from a front face of the first cabinet 10. As shown by FIG. 4, inside of the stocker 23 is partitioned in an up and down direction by a plurality of shelves 23a. Further, the incubation container 14 is made to be able to be contained in the stocker 23 horizontally. Further, a lowermost stage of the stocker 23 constitutes a space of arranging the container carrying in/out mechanism 25.

Figure 6:
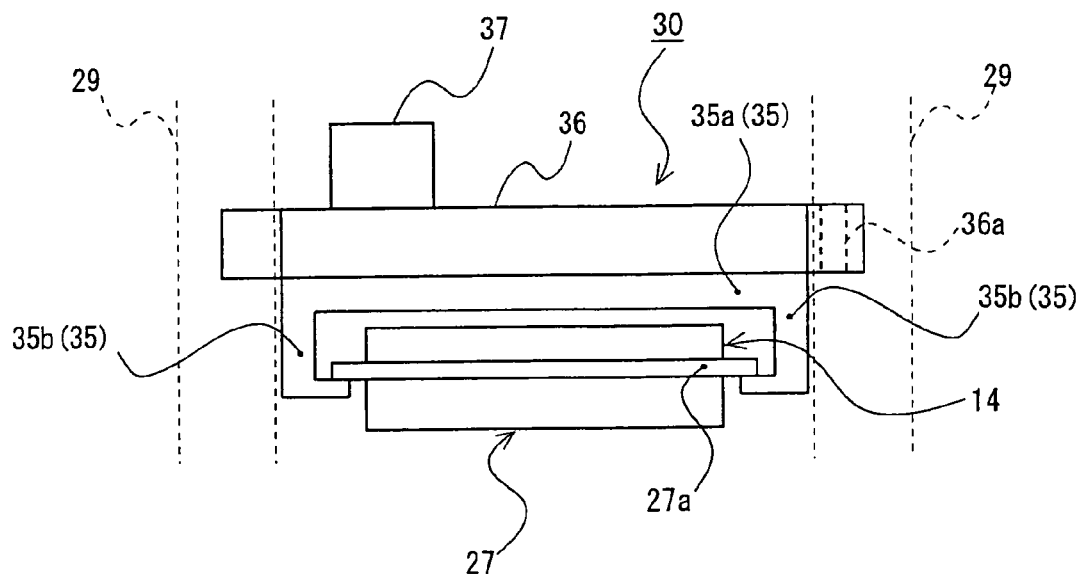
FIG. 6 is a front view showing a constitution of a carrying arm section.
Figure 7:
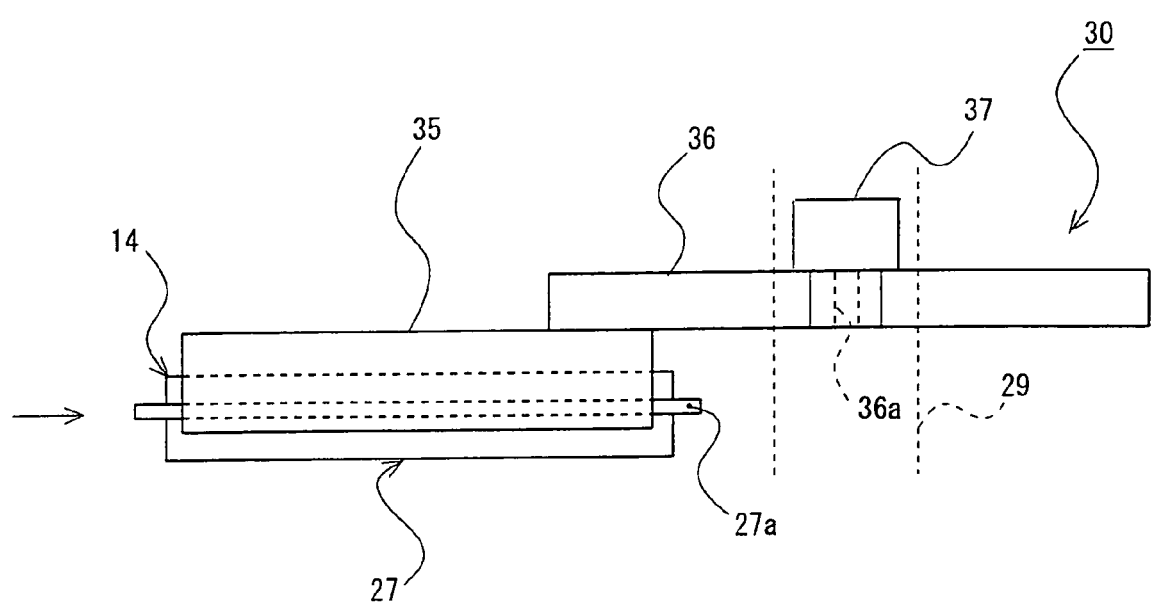
FIG. 7 is a side view showing the constitution of the carrying arm section.

Here, according to the first embodiment, in order to facilitate to carry the incubation container 14 by the container shifting mechanism 24, the incubation container 14 is handled by being mounted on a holder 27 in a shape of a tray. Further, an outer peripheral portion of the holder 17 is formed with a support piece 27a to direct to an outer side (refer to FIG. 6, FIG. 7).

The container shifting mechanism 24 is arranged at a center of inside of the temperature-controlled room 12 in view from the front face of the first cabinet 10. The container shifting mechanism 24 includes a base 28 in a rectangular shape prolonged in a front and rear direction, a vertical frame 29 extended in an up and down direction, and a carrying arm portion 30 for supporting the holder 27.

The base 28 is attached with the vertical frame 29 movably in a front and rear direction (Y direction). A position in Y direction of the vertical frame 29 is detected by a position sensor 31. Further, an outer side of the base 28 is fixed with a first motor 32 for driving the vertical frame 29 in Y direction.

The vertical frame 29 is configured by 2 pieces of guide rails arranged in parallel with each other. The carrying arm portion 30 is attached to between the vertical frames 29 movably in an up and down direction (Z direction). The carrying arm portion 30 is moved by a screw shaft (not illustrated) included in one of the vertical frames 39. Further, the vertical frame 29 is fixed with a second motor 33 for driving the carrying arm portion 30 in Z direction, and a position sensor 34 for detecting a position in Z direction of the carrying arm portion 30. Further, a position of the second motor 33 is changed in Y direction in accordance with movement of the vertical frame 29.

The carrying arm portion 30 includes a container supporting portion 35, a sliding mechanism portion 36, and a third motor 37. The container supporting portion 35 includes a main body portion 35a a width of which is set to be more or less wider than a width of a total of the holder 27 including the support piece 27a, and a set of hanging claws 35b formed at both side edges of the main body portion 35a. The hanging claws 35b are arranged opposedly to direct to an inner side on a lower side of the main body portion 35a. Further, an interval between front end portions of the hanging claws 35b is set to be slightly larger than a width of a main body portion of the holder 27 excluding the support piece 27a. Therefore, the container supporting portion 35 is made to be able to support the holder 27 by engaging the hanging claws 35b and the support piece 27a.

The sliding mechanism portion 36 is arranged on an upper face side of the container supporting portion 35. The sliding mechanism portion 36 slides the container supporting portion 35 in a left and right direction (X direction). By operating the sliding mechanism portion 36, the holder 27 mounted with the incubation container 14 is made to be able to be delivered and received between the stocker 23, the container carrying in/out mechanism 25 or the microscope unit 26 and the container shifting mechanism 24. Further, the sliding mechanism portion 36 includes a nut portion 36a screwed with the screw shaft of the vertical frame 29. Further, the sliding mechanism portion 36 is fixed with the third motor 37 for driving the container supporting portion 35 in X direction. Further, a position of the third motor 37 is changed in Y direction in accordance with movement of the vertical frame 29 and changed in Z direction in accordance with movement of the carrying arm portion 30.

The container carrying in/out mechanism 25 is installed at a vicinity of the carrying in/out entrance 15 at the lowermost stage of the stocker 23. The container carrying in/out mechanism 25 includes a carrying table 25a capable of mounting the holder 27, and a motor unit 25b for reciprocating the carrying table 25a to and from outside of the carrying in/out entrance 15.

The microscope unit 26 is arranged on a right side of inside of the temperature-controlled room 12 in view from the front face of the first cabinet 10. The microscope unit 26 includes a sample stage 38 for mounting the incubation container 14 and the holder 27, and an illumination apparatus 39 arranged in a state of being extended to an upper side of the sample stage 38. The microscope unit 26 is arranged by being fitted to the opening 10b of the bottom face of the first cabinet 10. Further, although the sample stage 38 and the illumination apparatus 39 are arranged at inside of the temperature-controlled room 12 of the first cabinet 10, most of the main body portion of the microscope unit 26 is contained to a side of the second cabinet 11. Here, the sample stage 38 is configured to be able to move the holder 27 in a horizontal direction (X direction and Y direction). Further, the illumination apparatus 39 illuminates the incubation container 14 from an upper side.

On the other hand, the main body portion of the microscope unit 26, and a controlling unit 40 are contained in the second cabinet 11.

Figure 8:
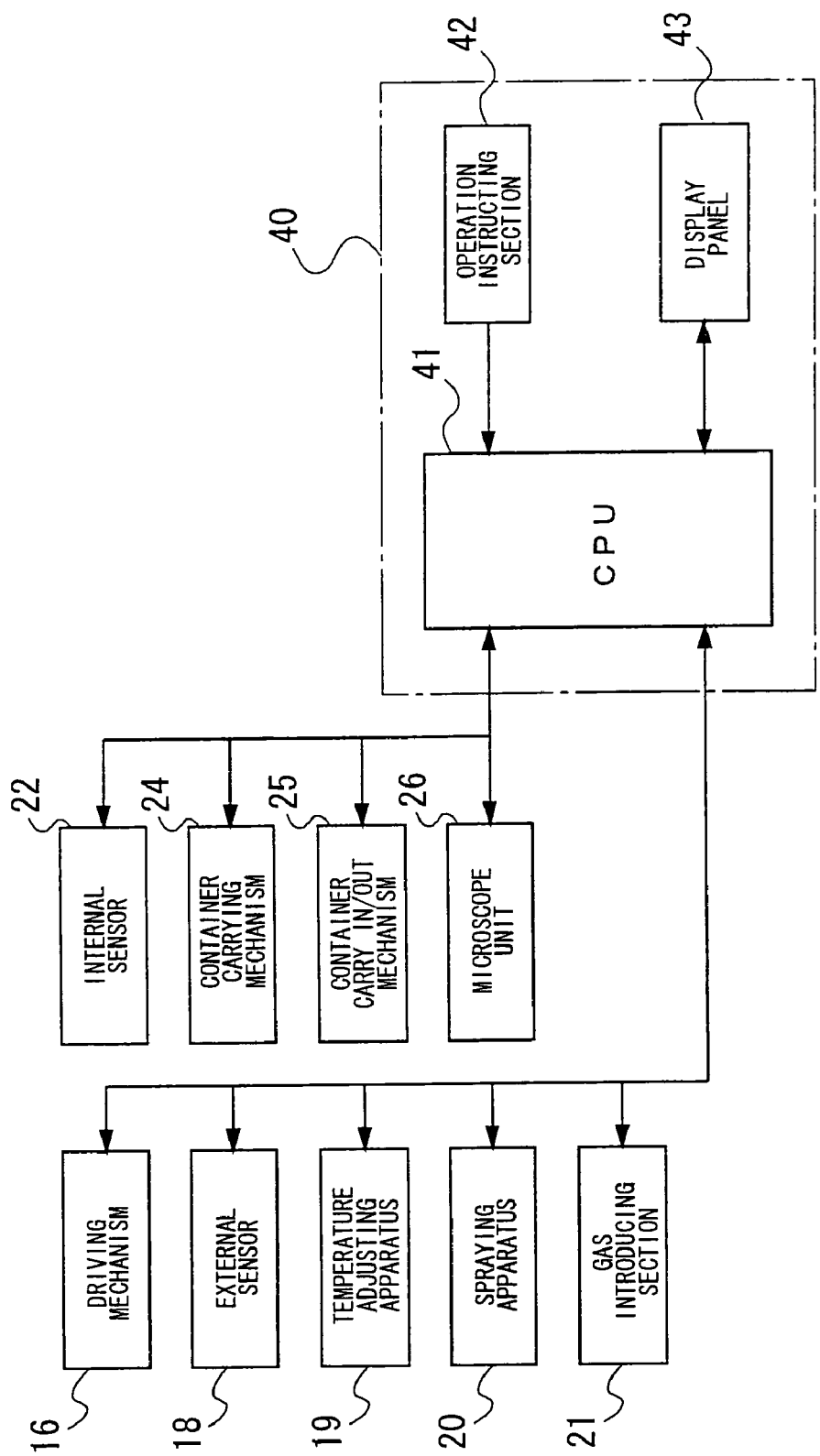
FIG. 8 is a block diagram of a control unit according to the first embodiment.

The control unit 40 includes CPU 41, an operation instructing section 42 and a display panel 43. Here, FIG. 8 is a block diagram showing a relationship between the controlling unit 40 and respective portions of the incubator. CPU 41 is connected to the driving mechanism 16, the external sensor 18, the temperature adjusting apparatus 19, the spraying apparatus 20, the gas introducing section 21, the internal sensor 22, the container carrying mechanism 24, the container carrying in/out mechanism 25, and the microscope unit 26. Further, CPU 41 controls the respective portions in accordance with a predetermined program.

The operation instructing section 42 includes inputting means of a keyboard or the like for operating the respective portions of the incubator by way of CPU 41. That is, CPU 41 executes operations of adjusting the environmental parameter of inside of the temperature-controlled room 12, carrying in/out the incubation container 14 to and from inside and outside of the temperature-controlled room 12, observing the sample of the incubation container 14 and carrying the incubation container 14 at inside of the temperature-controlled room 12 or the like. Here, instruction of the operation instructing section 42 includes both of instruction input directly from a user and instruction previously set by a program. Further, the display panel 43 outputs to display an environment condition or the like of the temperature-controlled room 12 input from CPU 41.

The operation of the incubator of the first embodiment will be explained as follows. Further, general operation of the respective portions of the incubator will briefly be explained.

When the incubator is operated, CPU 41 monitors the value of the environment parameters at inside of the temperature-controlled room 12 by the internal sensor 22. When there is a variation in the value of the environment parameter, CPU 41 operates any of the temperature adjusting apparatus 19, the spraying apparatus 20, and the gas introducing section 21 to adjust the value of the environment parameter at inside of the temperature-controlled room 12 to be constant.

When the incubation container 14 is instructed to carry from the operation instructing section 42, CPU respectively drives the respective motors 32, 33, 37 of the container carrying mechanism 24 to carry the incubation container 14 on the holder 27. At this occasion, the container carrying mechanism 24 executes any of (1) switching the incubation container 14 at inside of the stocker 23, (2) delivery of the incubation container 14 to the container in/out mechanism 25, (3) delivery of the incubation container 14 to the microscope unit 26.

When instructed to observe the incubation container 14 from the operation instructing section 42, CPU 41 observes the sample of the incubation container 14 by operating the microscope unit 26. At this occasion, CPU 41 illuminates the sample by the illumination apparatus 39 of the microscope unit 26. Further, CPU 41 moves the sample stage 38 in the horizontal direction in accordance with instruction from the operation instructing section 42. Thereby, the sample can be observed at an arbitrary position of the incubation container 14.

When the incubation container 14 is instructed to carry out from the operation instructing section 42, CPU 41 opens the automatic door 17 by operating the driving mechanism 16. Further, CPU 41 carries out the incubation container 14 and the holder 27 of the carrying table 25a to outside of the temperature-controlled room 12 by driving the motor unit 25b of the container carrying in/out mechanism 25. Similarly, when the incubation container 14 is instructed to carry in from the operation instructing section 42, CPU 41 carries in the incubation container 14 of the carrying table 25a and the holder 27 to inside of the temperature-controlled room 12 by driving the motor unit 25b of the container carrying in/out mechanism 25. Further, CPU 41 closes the automatic door 17 by operating the driving mechanism 16.

Next, an explanation will be given of an operation particular to the first embodiment. When the incubation container 14 is carried in/out, a sample is observed, the incubation container 14 is carried and the like by instruction of the operation instructing section 42 as described above, a variation in the environment parameter is brought about by a temperature rise by generating heat of the motor or the like, or making outside air flow in/out to and from the carrying in/out entrance 15. Therefore, according to the incubator of the first embodiment, CPU 41 executes the following control in the above-described case.

(Case of Operating Motor)

Figure 9:
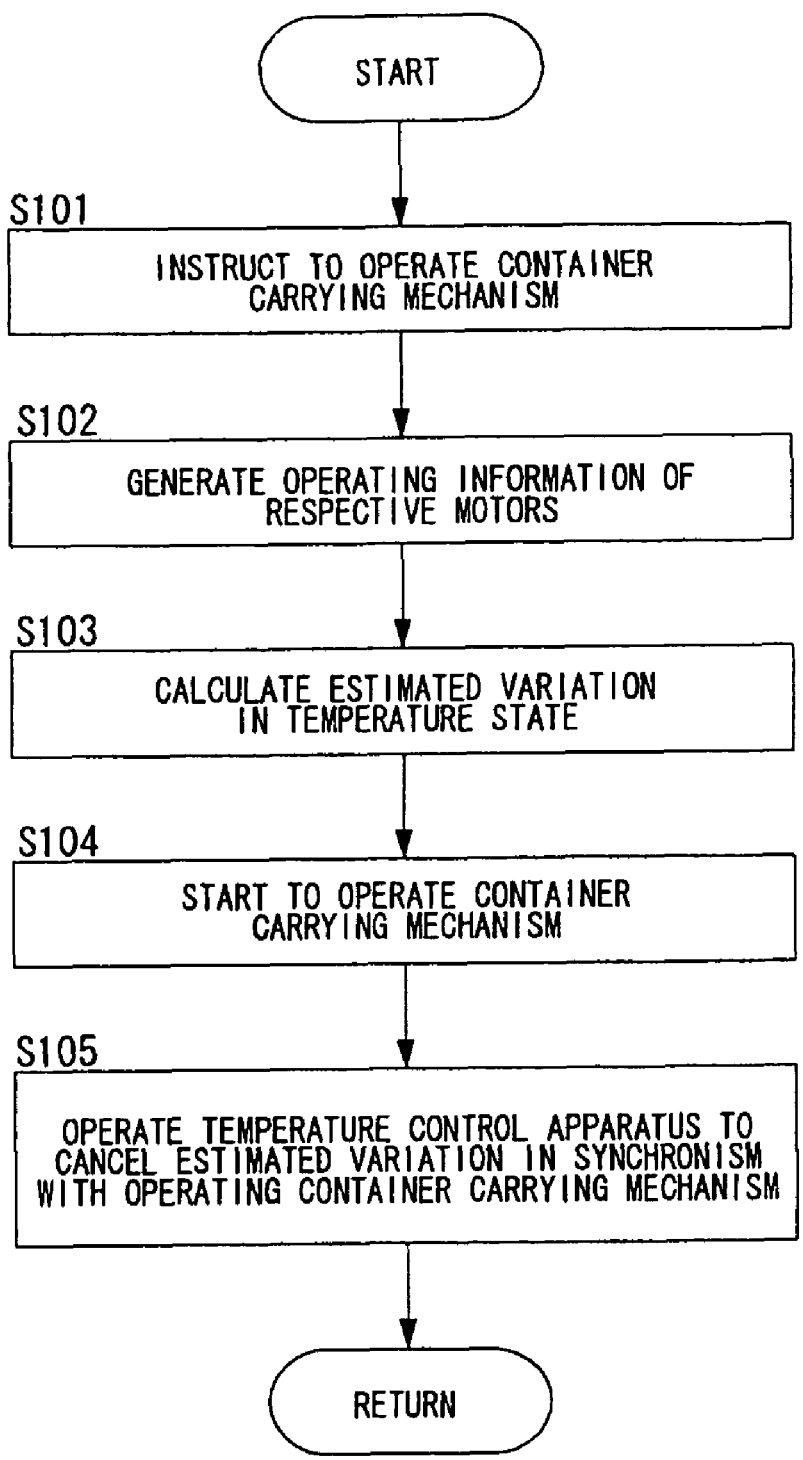
FIG. 9 is a flowchart showing a temperature control when a motor of the container carrying mechanism is operated.

FIG. 9 is a flowchart showing a temperature control in a case of operating the motors 32, 33, 37 of the container carrying mechanism 24. Further, although a similar temperature control is carried out also in operating the sample stage 38, operating the motor unit 25b of the container carrying in/out mechanism 25 and operating the driving mechanism 16 of the automatic door 17, a content thereof is substantially common to that of the case of FIG. 9 described below, and therefore, a duplicated explanation thereof will be omitted.

Step S101: the operation instructing section 42 instructs CPU 41 to operate the container carrying mechanism 24 in accordance with an input of a user or a predetermined program.

Step S102: CPU 41 generates operating information (position information and information of operating time) of the respective motors 32, 33, 37 of the container carrying mechanism 24 based on operation instruction of the operation instructing section 42. Here, the position information includes information of an initial position (position in starting operation) of the motor operated in the container carrying mechanism 24, and information of changing a position of the motor in accordance with operation of the container carrying mechanism 24. Further, the information of the operating time is shown by an amount in which the motor is operated and a time point in which the motor is operated, with reckoning from the start of operation of the container carrying mechanism 24.

For example, with regard to the position information, the first motor 32 is not moved, and therefore, CPU 41 generates only an initial position of the first motor 32 as position information. On the other hand, positions of the second motor 33 and the third motor 37 are moved in accordance with operation of the container carrying mechanism 24, and therefore, position information is generated as follows.

CPU 41 detects a current position of the second motor 33 from an output of the position sensor 31 and generates information of an initial position of the second motor 33. Further, CPU 41 generates information of an initial position of the third motor 37 by detecting a current position of the third motor 37 from outputs of the position sensors 31, 34.

Next, CPU 41 calculates a change in a position in Y direction of the second motor 33 based on the current position of the second motor 33 and a content of the operation instruction, and generates information of a change in a position of the second motor 33. Further, CPU 41 calculates information of changes in positions in Y direction, Z direction of the third motor 37 based on the current position of the third motor 37 and the content of the operation instruction, and generates information of a change in a position of the third motor 37. Note that, as information of the changes in the positions of the second motor 33 and the third motor 37, a plurality of pieces of position information in correspondence with a series of operation are generated at time intervals of predetermined seconds.

Step S103: CPU 41 calculates an estimated variation of a temperature state at inside of the temperature-controlled room 12 in a time period from starting to operate to finish operating the container carrying mechanism 24. Specifically, the estimated variation is calculated by a predetermined state equation based on the operation information of the respective motors (S102) and previously set heat generating amounts per unit time of the respective motors.

Further, the estimated variation is calculated for a plurality of respective divided regions pertinently set to inside of the temperature-controlled room 12 separately from each other. The estimated variations of the respective divided regions are respectively varied by position relationships of the motors constituting heat sources (initial position and movement of motor) and states of operating the motors (ON/OFF of motors at respective positions).

Step S104: CPU 41 operates the respective motors of the container carrying mechanism 24 based on operation instruction of the operation instructing section 42.

Step S105: CPU 41 controls the respective temperature adjusting apparatus 19 respectively independently from each other to cancel the estimated variations (S103) in the temperature states in synchronism with the operation of the container carrying mechanism 24. Thereby, even in operating the motors, the temperature state at inside of the temperature-controlled room 12 is maintained substantially uniformly. Further, CPU 41 finishes controlling the respective temperature adjusting apparatus along with finishing the operation of the container carrying mechanism 24 to recover to a normal temperature control state. The explanation of the example of FIG. 9 has been finished.

(Case of Temperature Control by Operation of Illumination Apparatus)

Figure 10:
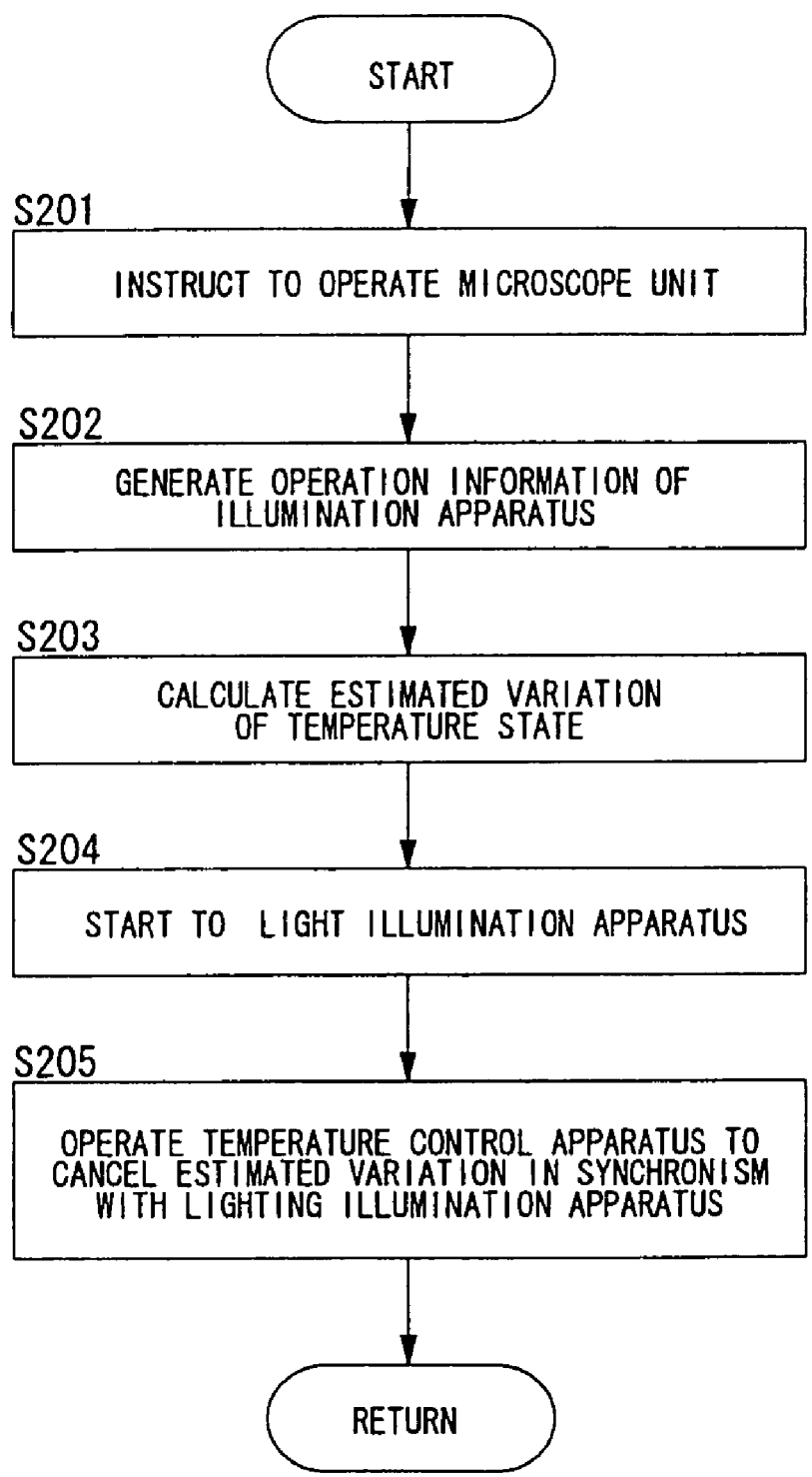
FIG. 10 is a flowchart showing a temperature control when an illumination apparatus of a microscope unit is operated.

FIG. 10 is a flowchart showing a temperature control in a case of operating the illumination apparatus 39 of the microscope unit 26.

Step S201: the operation instructing section 42 instructs CPU 41 to operate to observe the sample in accordance with the input of the user or the predetermined program.

Step S202: CPU 41 generates operation information of the illumination apparatus 39 (information of arranging the illumination apparatus 39 and information of illumination time) based on operation instruction of the operation instructing section 42.

Step S203: CPU 41 calculates an estimated variation of the temperature state at inside of the temperature-controlled room 12 in a time period from starting to operate to finish operating the illumination apparatus 39. Specifically, CPU 41 calculates the estimated variation by a predetermined state equation based on the operation information of the illumination apparatus 39 (S202) and a previously set heat generating amount per unit time of the illumination apparatus 39.

Further, the estimated variations are calculated for a plurality of respective divided regions pertinently sets at inside of the temperature-controlled room 12 separately from each other. Further, the estimated variations of the respective divided regions are respectively varied by distances from the illumination apparatus 39 and illumination time.

Step S204: CPU 41 lights the illumination apparatus 39 based on operation instruction of the operation instructing section 42. Further, CPU 41 executes observation of the sample by the microscope unit 26.

Step S205: CPU 41 controls the respective temperature adjusting apparatus 19 independently from each other to cancel the estimated variations of the temperature state (S203) in synchronism with lighting the illumination apparatus 39 at S204. Thereby, even in lighting the illumination apparatus 39, the temperature state at inside of the temperature controlled room 12 is maintained substantially uniformly. Further, CPU 41 finishes controlling the respective temperature adjusting apparatus 19 at S205 after finishing the operation of the container carrying mechanism 24 and recovers to normal temperature control state. The explanation of the example of FIG. 10 has been finished.

(Case of Environment Parameter Control by Opening Carrying In/Out Entrance)

Figure 11:
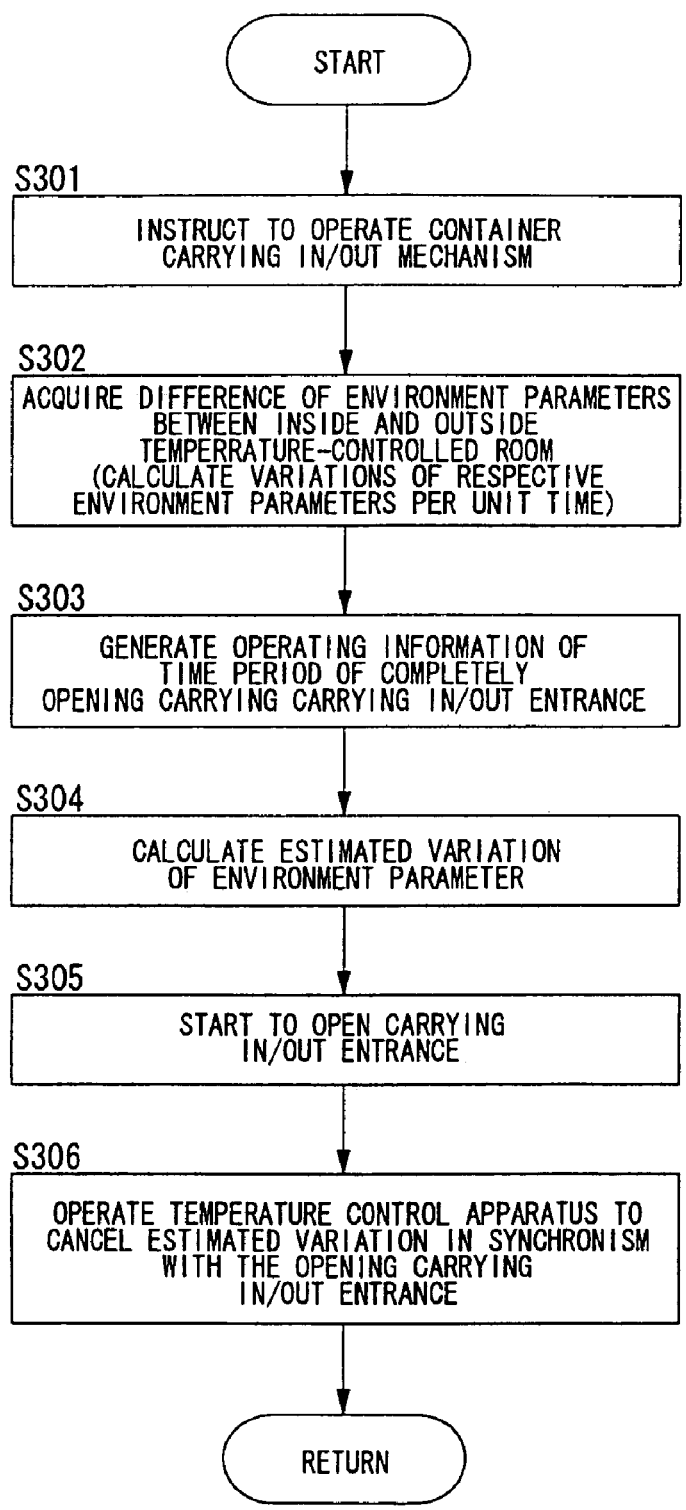
FIG. 11 is a flowchart showing an example of an environment parameter control by opening a carrying in/out entrance.

FIG. 11 shows a flowchart showing an example of an environment parameter control by opening the carrying in/out entrance 15. In the example of FIG. 11, an explanation will be given of a case of adjusting a temperature, humidity and a carbon dioxide carbon concentration. Further, when an oxygen concentration and a nitrogen concentration are adjusted, in the example of FIG. 11, a content thereof is substantially common to a case of adjusting the carbon dioxide concentration, and therefore, a duplicated explanation thereof will be omitted.

Step S301: the operation instructing section 42 instructs CPU 41 to operate to carry out the container (or carry in the container) in accordance with an input of a user or a predetermined program.

Step S302: CPU 41 respectively acquires values of environment parameters (temperature, humidity, and carbon dioxide concentration) at inside and outside of the temperature-controlled room 12 by the external sensor 18 and the internal sensor 22. Further, CPU 41 respectively calculates variation amounts of the respective environment parameters per unit time based on differences of values of the respective environment parameters at inside and outside of the temperature-controlled room 12.

Step S303: CPU 41 generates information of a time period of completely opening the carrying in/out entrance 15 (a time period of completely opening the carrying in/out entrance) based on operation instruction of the operation instructing section 42.

Step S304: CPU 41 respectively calculates estimated variations of the respective environment parameters at inside of the temperature-controlled room 12 during a time period from opening to closing the carrying in/out entrance 15. Specifically, CPU 41 calculates estimated variations of the respective environment parameters by a predetermined state equation based on (1) the variations of the respective environment parameters per unit time (S302), (2) the time period of completely opening the carrying in/out entrance 15 (S303), (3) an opening area of the carrying in/out entrance 15. Further, it is further preferable that CPU 41 calculates the estimated variations of the respective environment parameters also with regard to an amount thereof in opening and closing the automatic door 17 based on information of necessary times in opening and closing the carrying in/out entrance 15 and an opening and closing speed of the automatic door 17.

Step S305: CPU 41 opens the carrying in/out entrance 15 by operating the driving mechanism 16 of the automatic door 17 based on operation instruction of the operation instructing section 42. Further, CPU 41 carries out the carrying table 25a to outside of the temperature-controlled room 12 by operating the motor unit 25b of the container carrying in/out mechanism 25.

Step S306: CPU 41 operates the temperature adjusting apparatus 19, the spraying apparatus 20 and the gas introducing section 21 to cancel the estimated variations of the environment parameters (S304) in synchronism with the opening operation of the carrying in/out entrance 15 at S305. Thereby, even in opening the carrying in/out entrance 15, the temperature, the humidity, the carbon dioxide concentration at inside of the temperature-controlled room 12 are substantially maintained to be uniform. Further, CPU 41 finishes the above-described control of the temperature adjusting apparatus 19 and the like by finishing closing the automatic door to recover to the normal control state. The explanation of the example of FIG. 11 has been finished.

Further, although in the explanation of FIG. 9 through FIG. 11 mentioned above, an explanation has been given of only a case of carrying out the respective operations respectively by themselves for convenience of explanation, actually, there is also a case in which the above-described plurality of operations are progressed simultaneously. For example, when the sample is observed by the microscope unit 26, there is a case of simultaneously carrying out illumination of the illumination apparatus 39 and operation of the sample base 28, in this case, the control of canceling the heat generation of the illumination apparatus 39 and the control of canceling heat generation of the motor of the sample stage 38 are substantially simultaneously carried out. Further, according to the first embodiment, a heating function and a cooling function are higher in the temperature adjusting apparatus 19 at a vicinity of a region of arranging the microscope unit 26 than in the temperature adjusting apparatus at other position, and therefore, also in such a case, the temperature at a vicinity of the microscope unit 26 can be adjusted similar to normal.

An effect of the incubator according to the first embodiment will be explained as follows.

(1) According to the first embodiment, when the respective motors of the container carrying apparatus 24, the sample stage 38 of the microscope unit 26, the motor unit 25b of the container carrying in/out mechanism 25 or the driving mechanism 16 of the automatic door 17 are operated, CPU 14 calculates the estimated variation of the temperature state (S103). Further, the temperature adjusting apparatus 19 controls the temperature at inside of the temperature-controlled room 12 to cancel the estimated variation in synchronism with the operation of the motor (S105).

Therefore, according to the first embodiment, a time difference between starting to operate the motor and staring the temperature control becomes extremely small, the temperature control in accordance with the amount of generating heat of the motor is carried out, and therefore, the temperature change amount at inside of the temperature-controlled room 12 is considerably reduced. That is, according to the incubator of the first embodiment, it can comparatively easily be realized that while automatically carrying the incubation container 14 at inside of the temperature-controlled room 12, the temperature environment at inside of the temperature-controlled room 12 can be maintained substantially constant.

Particularly, according to the first embodiment, the plurality of temperature adjusting apparatus 19 control the temperature at inside of the temperature-controlled room 12 independently from each other in consideration of the position of the operated motor (S103, S105). Further, when the positions of the motors are moved (the second motor 33 and the third motor 37 and the like), the temperature control at inside of the temperature-controlled room 12 is executed also in consideration of movement of the motors (S102, S103). Therefore, a nonuniformity in the temperature at inside of the temperature-controlled room 12 is significantly restrained from being brought about.

(2) According to the first embodiment, CPU 41 calculates the estimated variation of the temperature state when the illumination apparatus 39 illuminates the microscope unit 26 (S203). Further, the temperature adjusting apparatus 19 controls the temperature at inside of the temperature-controlled room 12 to cancel the estimated variation in synchronism with the operation of the illumination apparatus 39 (S205).

Therefore, a time difference between starting to illuminate of the illumination apparatus 39 and starting the temperature control becomes extremely small, the temperature control is carried out in accordance with the heat generating amount of the illumination apparatus 39, and therefore, the temperature change amount at inside of the temperature-controlled room 12 is considerably reduced. That is, according to the incubator of the first embodiment, it can comparatively easily be realized that when the sample is observed by the microscope at inside of the temperature-controlled room 12, the temperature environment at inside of the temperature-controlled room 12 is maintained substantially constant.

(3) According to the first embodiment, CPU 41 calculates the estimated variations of the respective environment parameters when the carrying in/out entrance 15 is opened (S304). Further, the temperature adjusting apparatus 19 and the like control the environment parameter at inside of the temperature-controlled room to cancel the estimated variation in synchronism with opening of the abovementioned carrying in/out entrance 15 (S306).

Therefore, according to the first embodiment, a time difference between opening of the carrying in/out entrance 15 and starting to control the respective environment parameters becomes extremely small, the environment condition is controlled in accordance with the variations of the environment parameters by opening the carrying in/out entrance 15, and therefore, the change amount of the environment condition at inside of the temperature-controlled room 12 is considerably reduced. That is, according to the incubator of the first embodiment, when the incubation container 14 is automatically carried in and out to and from the temperature-controlled room 12, it can comparatively easily be realized that the temperature environment at inside of the temperature-controlled room 12 is maintained substantially constant.

(Explanation of Second Embodiment)

Figure 12:
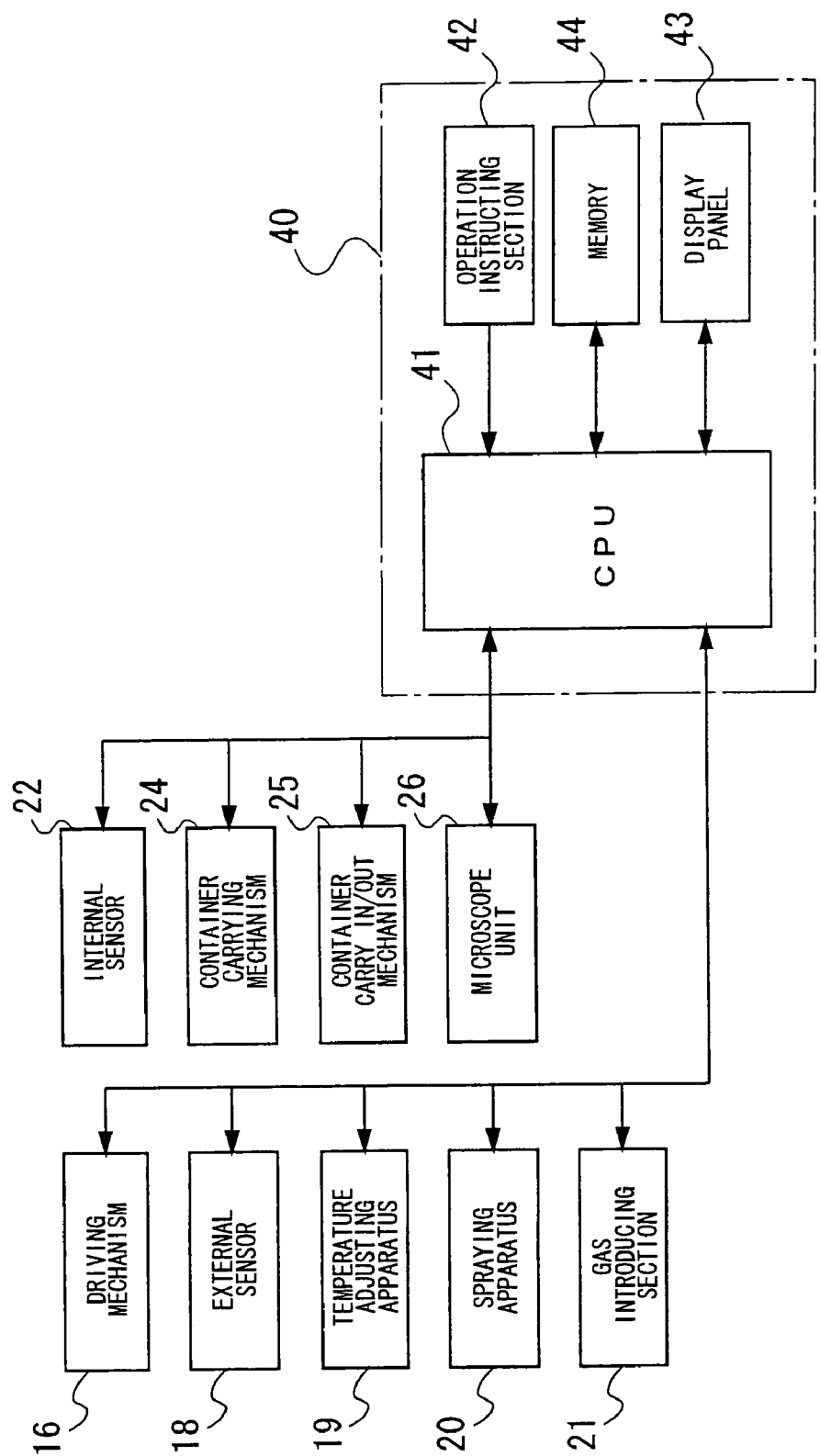
FIG. 12 is a block diagram of a control unit according to a second embodiment.

FIG. 12 is a block diagram showing a relationship between the control unit 40 and respective portions of the incubator according to a second embodiment. The second embodiment is a modified example of the first embodiment and constitutions other than the control unit 40 are substantially common to those of the first embodiment. Therefore, constitutions common to those of the first embodiment in the second embodiment are attached with the same notations and a duplicated explanation thereof will be omitted.

According to the control unit 40 of the second embodiment, a memory 44 is connected to CPU. The memory 44 is stored with (1) a look up table (LUT) showing a corresponding relationship between the operating information of the respective motors and the estimated variation of the temperature state, (2) LUT showing a corresponding relationship between the operating information of the illumination apparatus 39 and the estimated variation of the temperature state, (3) LUT showing a corresponding relationship between the variation amounts of the respective environment parameters per unit time and the time period of completely opening the carrying in/out entrance 15 and the estimated variations of the environment parameters.

Here, in LUT of the above-described (1), LUT in correspondence with the respective motors of the incubator is prepared. Further, in LUT of the above-described (3), LUT respectively in correspondence with the environment parameters controlled is prepared.

According to the second embodiment, CPU 41 acquires the estimated variation by LUT of the memory 44. Therefore, according to the second embodiment, in addition to an effect substantially similar to that of the first embodiment, a reduction in a calculating load of CPU 41, a simplification of a circuit scale of CPU 41 and the like can be realized. Further, according to the second embodiment, a variation in the actual environment parameter can be sampled by the internal sensor 22 in operating the motor and CPU 41 can correct data of LUT of the memory 44 based on a measured value.

Supplementary Item of Embodiment

Although an explanation has been given of the invention by the above-described embodiments as mentioned above, the technical range of the invention is not limited to the above-described embodiments but may be configured by, for example, following modes.

(1) An incubator of the invention is not limited to the constitution capable of adjusting all of the carbon dioxide concentration, oxygen concentration and the nitrogen concentration. Also an incubator capable of adjusting any one or two of the carbon dioxide concentration, the oxygen concentration and the nitrogen concentration can naturally be included in the technical range of the invention.

(2) The constitutions of the respective portions of the invention are not limited to the embodiments. For example, the temperature adjusting apparatus of the invention may be realized by other publicly-known apparatus of a combination of a heater unit and a refrigerant circulating system or the like. Further, the environment parameter adjusting section of adjusting the humidity according to the invention may be configured by a humidifying dish storing humidifying water and a temperature adjusting apparatus for controlling a water temperature of the humidifying dish (illustration of both is omitted).

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents maybe resorted to, falling within the scope thereof.

The invention claimed is:

1. An environment controlling method of an incubator which includes a temperature-controlled room configured to be adjusted to a predetermined environment condition and to culture therein a sample of an incubation container, the incubator further including a carrying mechanism within said temperature-controlled room, having a driving source, and carrying said incubation container based on instruction information, the environment controlling method comprising the steps of:
  an operation instructing step providing instruction information for moving a position of said incubation container within said temperature-controlled room;
    an operation information generating step receiving said instruction information from said operation instructing step and generating, via an operation information generating unit, operation information which is a spatial operating position of said driving source within said temperature-controlled room being predicted based on said instruction information prior to a carrying operation of said carrying mechanism;
  an estimated variation outputting step receiving said operation information from said operation information generating step and outputting an estimated variation of temperature state of said temperature-controlled room by operating said driving source based on the operation information and a heat generating amount per unit time of said driving source;
  a temperature adjusting step receiving said operation information from said operation information generating step and adjusting a temperature within said temperature-controlled room by using at least one temperature adjusting section and an output of a sensor placed inside said temperature-controlled room; and
  a temperature controlling step receiving said operation information from the operation information generating step and controlling said temperature adjusting section to cancel a temperature change of an amount of said estimated variation in synchronism with operating said driving source.

2. The environment controlling method of claim 1, wherein:
  a plurality of said temperature adjusting sections are arranged at positions inside of said temperature-controlled room different from each other, and
  outputs of the respective temperature adjusting sections change independently from each other based on said operation information within said temperature-controlled room.

3. The environment controlling method of claim 1, wherein said driving source is a motor, and
  said operation information generating unit generates operation information regarding an operating position and operation time of said motor.

4. The environment controlling method of claim 1, wherein said estimated variation outputting step is configured either by a recording section recorded with a corresponding relationship between said operation information and said estimated variation or by a calculating section calculating said estimated variation based on said operation information and a heat generating amount per unit time of said driving source in which said calculating section divides a space within the temperature-controlled room into a plurality of regions and calculates said estimated variation for the respective divided regions.

5. An environment controlling method of an incubator system which includes an incubator which has a temperature-controlled room configured to be adjusted to a predetermined environment condition and to culture therein a sample of an incubation container, an illuminating light source configured to illuminate said incubation container from inside of said temperature-controlled room, at least one temperature adjusting section configured to adjust a temperature inside of said temperature-controlled room, and an incubator controlling section configured to control said incubator, the environment controlling method comprising the steps of:
  an operation instructing step instructing illumination of said illuminating light source;
  an operation information generating step receiving instruction information from said operation instructing step and generating operation information regarding an operating time period of said illuminating light source prior to operating said illuminating light source;
  an estimated variation outputting step receiving said operation information from said operation information generating step and outputting an estimated variation of a temperature state within said temperature-controlled room by operating said illuminating light source based on said operation information, a heat generating amount per unit time of said illuminating light source, and a distance from said illuminating light source; and
  a controlling step receiving said operation information from said operation information generating step and controlling said temperature adjusting section to cancel a temperature change of an amount of said estimated variation in synchronism with operating said illuminating light source.

6. The environment controlling method according to claim 5, wherein:
  a plurality of said temperature adjusting sections are arranged at positions inside of said temperature-controlled room different from each other, and
  said controlling step sets at least a temperature adjusting section arranged at a region in a vicinity of said illuminating light source to be higher in a temperature changing function than a region at another position.

7. The environment controlling method according to claim 5, wherein:
said estimated variation outputting step is configured either by a recording section recorded with a corresponding relationship between said operation information and said estimated variation or by a calculating section calculating said estimated variation based on said operation information, the heat generating amount per unit time of said illuminating light source, and the distance from said illuminating light source.

8. An environment controlling method of an incubator system including an incubator which has a temperature-controlled room configured to be adjusted to a predetermined environment condition and to culture therein a sample of an incubation container, a carrying in/out entrance of said incubator configured to carry in and out said incubation container to and from inside of said temperature-controlled room, an automatic door of said incubator configured to open and close said carrying in/out entrance, first and second sensor sections for acquiring a value of said environment parameter on an inner side and an outer side, respectively, of said temperature-controlled room and an incubator controlling section configured to control said incubator, the environment controlling method comprising the steps of:

an environment parameter adjusting step adjusting an environment parameter selected from any one of a temperature, a humidity, a carbon dioxide concentration, an oxygen concentration and a nitrogen concentration inside of said temperature-controlled room;

a first sensor step acquiring the value of said environment parameter on an inner side of said temperature-controlled room;

a second sensor step acquiring the value of said environment parameter on an outer side of said temperature-controlled room;

an operation instructing step providing instructions for various operations of said incubator;

an operation information generating step receiving said instruction information from said operation instructing step and generating operation information with regard to a time period of opening said automatic door prior to operating said automatic door;

an estimated variation outputting step receiving said operation information from said operation instructing step and outputting an estimated variation of said environment parameter within said temperature-controlled room by opening said automatic door based on a difference of said environment parameter between the inside and the outside of said temperature-controlled room, said operation information, an opening area of said automatic door and a variation of said environment parameter per time unit; and a parameter controlling step receiving said operation information from said operation information generating step and controlling said environment parameter adjusting step to cancel a change in said environment parameter of an amount of said estimated variation in synchronism with operating said automatic door.

9. The environment controlling method according to claim 8, wherein
said estimated variation outputting step is configured either by a recording section recorded with a difference of said environment parameters between inside and outside of said temperature-controlled room and a corresponding relationship between said operation information and said estimated variation, or by a calculating section calculating said estimated variation based on the difference of said environment parameters between inside and outside of said temperature-controlled room, said operation information, the opening area of said automatic door, and the variation of said environment parameter per time unit.

* * * * *